US006832983B2

(12) United States Patent
Goodman

(10) Patent No.: US 6,832,983 B2
(45) Date of Patent: Dec. 21, 2004

(54) ARTICLE OF CLOTHING WITH A NOVEL ATTACHMENT MEANS

(76) Inventor: John Mott Goodman, 9472 Central Ave., Garden Grove, CA (US) 92844-1505

(*) Notice: Subject to any disclaimer, the term of this patent is extended or adjusted under 35 U.S.C. 154(b) by 128 days.

(21) Appl. No.: 10/113,522

(22) Filed: Apr. 1, 2002

(65) Prior Publication Data

US 2003/0187323 A1 Oct. 2, 2003

(51) Int. Cl.[7] .................... A61F 5/00
(52) U.S. Cl. .................... 600/38; 2/67; 2/69; 2/300
(58) Field of Search .................... 600/38–41; 128/846, 128/885, 886; 2/4, 67, 69, 78.1, 1, 455, 456, 406, 309, 247

(56) References Cited

U.S. PATENT DOCUMENTS 4,966,165 A 10/1990 Anderson
5,181,527 A 1/1993 Dorsey et al.
5,347,657 A 9/1994 Unsell
5,690,603 A 11/1997 Kain
6,129,083 A 10/2000 Jansen
6,173,449 B1 1/2001 Osterrath

FOREIGN PATENT DOCUMENTS

FR 2647313 A 11/1990
WO WO 96/26700 A 9/1996

*Primary Examiner*—John P. Lacyk

(57) ABSTRACT

An article of clothing including extensions for insertion into a body cavity permit swimsuits, undergarments, and several other types of clothing to be secured in place with a minimum of fabric, as described. The articles are made dimensionally stable to maintain their position and orientation relative to the wearer's body.

3 Claims, 7 Drawing Sheets

ARTICLE OF CLOTHING WITH A NOVEL ATTACHMENT MEANS

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, TABLE, OR COMPUTER PROGRAM

Not Applicable

BACKGROUND OF INVENTION

People wear clothing for three principal reasons:

(1) To protect themselves from the environment, (2) for modesty, and (3) To respond to the dictates of fashion.

To accomplish any of these purposes, it is vital that the garments do not fall off of one's body. And for that to be insured, they must have a certain degree of mechanical integrity internally, and they must be made in some fashion that permits taking advantage of various anatomical features of a person's body in one way or another.

There have been, to date, only four general methods used, singly or in combination, to accomplish this vital task of keeping garments on the wearer's body. These methods may be termed wrapping, clamping, draping, and gluing. My invention presents a novel fifth means for securing garments on the wearer's body—one that is particularly appropriate for use in swimwear and underwear, but which may also find utility in many other types of garment.

Applicant has uncovered no means for retaining a garment on a wearer's body other than the four specified above [wrapping, clamping, draping, and gluing].

The purposes for holding garments on one's body are, as stated above, to protect one from the environment, for modesty, and to conform to the dictates of fashion. And, of course, to avoid losing them altogether.

Modesty or decency are terms that vary by culture. But in almost all cultures the minimum requirements include covering the external genitalia [penis and testicles for men, and vaginal lips for women], plus the anus. In many cultures women are also required to cover their breasts (at least the nipples and areolae). Some cultures require more coverage than this minimum, but for swimwear and underwear in particular, any such additional coverage is fast becoming optional.

The thong is a well-known variation on the bikini in which most of the back panel of the bottom is removed, and in the most extreme versions includes only a narrow strap connecting the bottom of the front panel down underneath the crotch and up to the waist band.

Like all swimsuits before them, the bikini, thong, and other similar swimsuit designs depend entirely on the principle of wrapping [and to the extent that the material is stretchy, on clamping] to keep the suit on the wearer's body.

BRIEF SUMMARY OF INVENTION

In accordance with the principles of the invention, garments include one or more extension(s) of a design that permits the extension to be inserted into a bodily orifice [or into more than one orifice at once]. For swimsuits and underpants, for example, the orifice to be used would be one's anus [or in the case of a woman, her vagina and/or her anus]. The extension is secured to the garment in a manner such that its location and orientation to the rest of the garment is maintained—generally by attaching the extension to a somewhat stiff frame. The frame is then wrapped by the fabric of the garment. In the case of swimsuits or underpants, the frame can usefully be extended to wrap around the pelvis from a small distance above the pubis to just behind the anus—thereby gaining added leverage from its snapped-in extension.

This strategy provides the garment with a secure means of mechanical anchorage to the wearer's body. Any article of apparel, of any design, that utilizes this means for assisting in keeping it on the wearer's body is included within the scope of this invention.

In some embodiments of this invention a "one-sided snap" feature is provided. This means that in the putting on of the garment, one would, in essence, "snap" it into a bodily orifice, and to take it off one would un-snap it from that orifice. As with ordinary snap fasteners, this implies that during the snapping and unsnapping process, the piece being inserted and/or the object into which it is inserted distorts in shape temporarily, with the insert finally occupying a wider space than the opening through which it was pushed. But in sharp contrast to ordinary snap fasteners in which one connects two portions of the snap fastener together or separates them, in order to close or open a gap in the garment, in this case one side of the "snap" is a part of the wearer's bodily anatomy.

BRIEF DESCRIPTION OF THE SEVERAL VIEWS OF THE DRAWING

Like components of the various embodiments herein are designated by the same numerals in all the figures to facilitate comparisons between those figures.

DETAILED DESCRIPTION OF THE INVENTION

In this section I shall describe in detail several preferred embodiments of my invention, and further I shall mention several additional useful embodiments, and I shall detail some of the benefits of using this invention in these ways.

Figure 1:
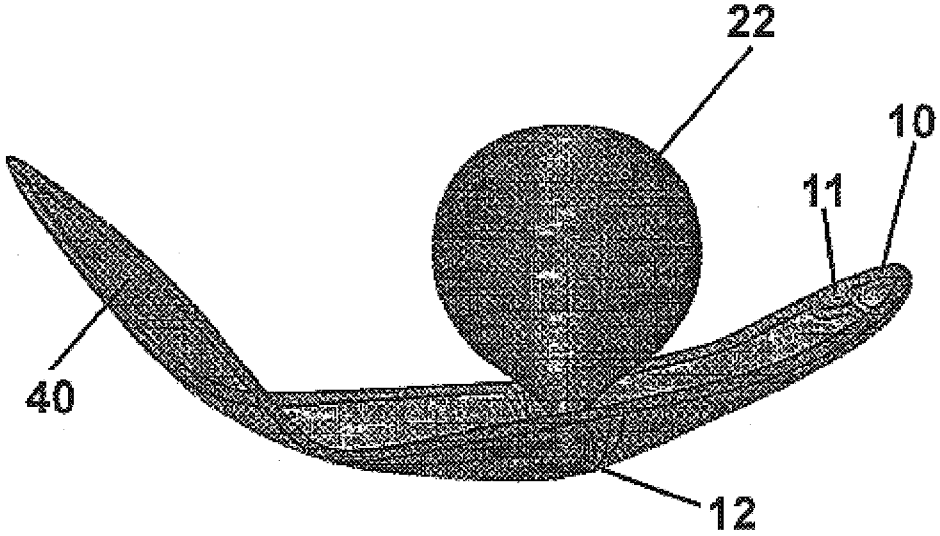
FIG. 1 shows a woman's swimsuit bottom utilizing this invention as the only means of garment attachment. In the example shown here, the garment extension is meant for insertion into a woman's vagina, and it attaches to a frame in order to hold the remainder of the garment against the contours of her pelvis. Here, and in FIG. 4 and FIG. 5, the garment fabric is rendered as if it were translucent, in order to reveal the details of the frame and extension construction.

FIG. 1 shows a woman's bathing suit bottom in accordance with the principles of this invention. The extension (22) shown is for vaginal insertion, and it attaches to semi-rigid frame (10) at the vaginal-insert attachment point (12). The frame extends rearward past the anus. An optional attachment point (11) is provided for use with an anal-insert extension-in addition to, or instead of—the vaginal-insert extension. The front end of the frame extends forward and up, conforming to the front of the pelvis, ending just past the pubis. The frame surrounds the vaginal lips and anus, and it bears on the front and crotch surfaces of the pelvis plus a portion of the inner surfaces of the buttocks. It does not bear on the inside of the woman's legs. The frame is slipped into a pocket formed in the fabric (40) which makes up the visible portion of the garment, which thus appears to be quite like a normal bathing suit, albeit a very small one with no obvious means of support.

Figure 9:
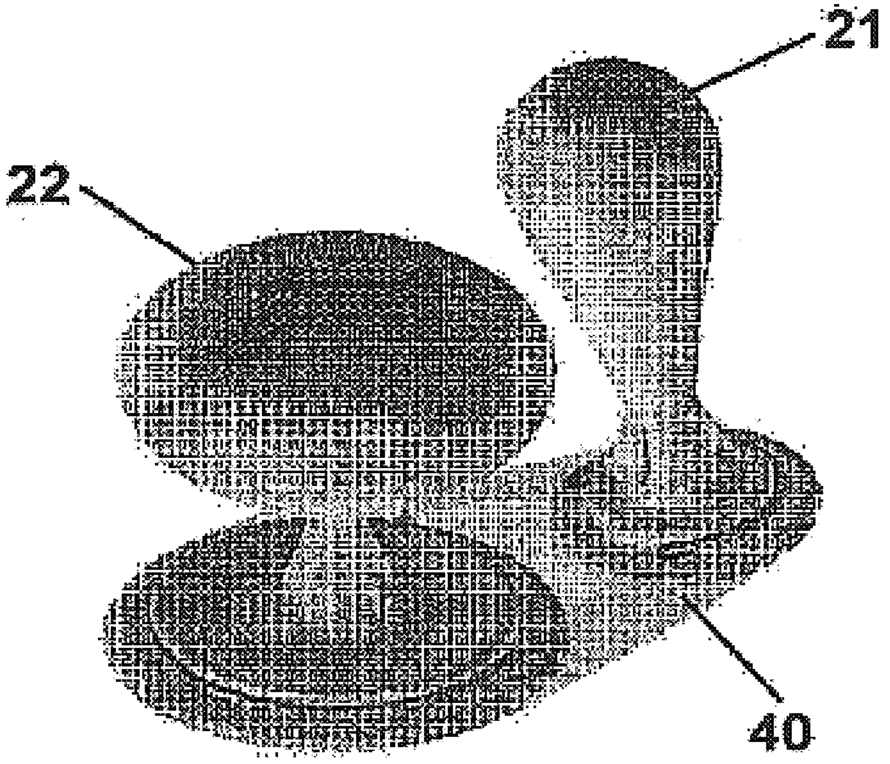
FIG. 9 shows another variation of the garment in FIG. 1, with two inserted extensions, suitable for insertion into both the wearer's vagina and her anus. This design provides minimum coverage with maximum security.

If a woman shaves off all of her pubic hair, a considerably smaller swimsuit can be constructed and still meet all of the normal requirements for decency. FIG. 9 shows one such design, in this case one which does not require any frame at all. Here there are two extensions to the garment, one adapted for insertion into the vaginal orifice (22) and one adapted for insertion into the anal orifice (21). Since each such extension covers the orifice into which it is inserted plus a small amount of skin around that orifice, and each holds one end of the very small fabric panel (40) spanning the two orifices, this design meets all the requirements of minimal decency without needing anything other than the fabric panel and the two inserted extensions. Furthermore, this design is doubly-secure against any inadvertent indecent exposure, inasmuch as it is held to the body in two separate, but closely-spaced locations.

Having the frame readily removable from the fabric permits several benefits of interest especially to people wishing to use the swimsuit while traveling. These include (a) ease of cleaning all the parts separately, (b) interchangeable coverings—which implies being able to carry a multitude of bathing suits with only one frame and its extension (s), in a very small space, at low cost, and with minimal weight. Not all the covering fabric forms need be of the same design—for example, the various suits shown in FIG. 5, FIG. 6, and FIG. 7 all use the same frame as the one in FIG. 1.

Since the suit in FIG. 1 has only the one point of attachment to the body, it is important that it maintain its shape and that it remain in a fixed orientation relative to the extension. The frame and its attachment points [shown in FIG. 2 without the extension or covering fabric, for greater clarity] in concert with the design of the vaginal-insert extension [detailed in FIG. 3(*a*)] provides these features.

Figure 2:
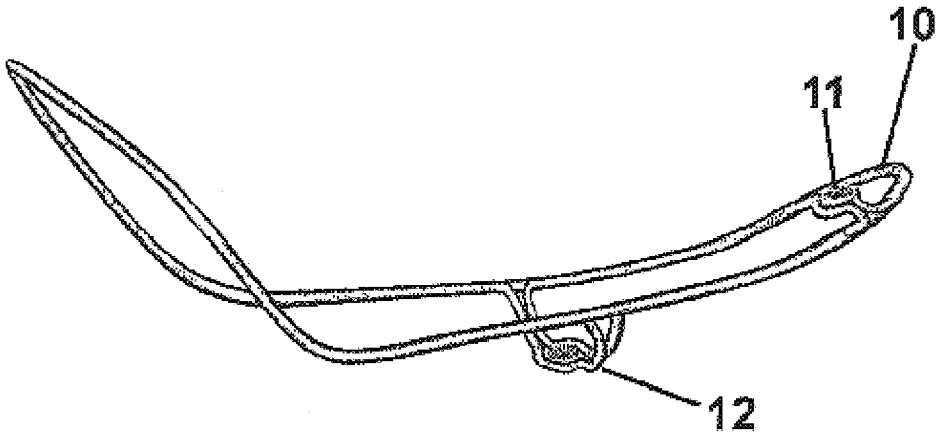
FIG. 2 shows the frame alone, without the fabric covering or the extension, in order to make the frame's construction fully evident.
Figure 3A:
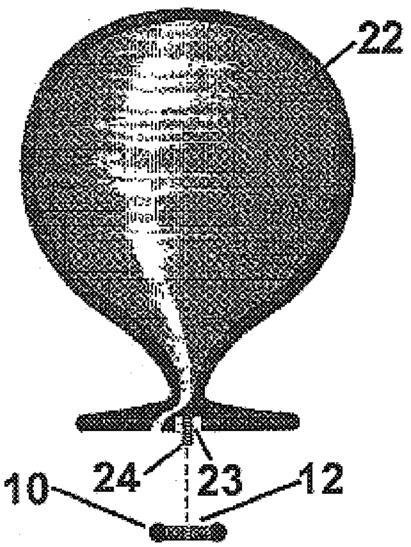
FIG. 3(*a*) shows in cross-section view the central portion of the frame and extension for the garment in FIG. 1. This only shows one way that a vaginal-insert extension might be formed. Some other possibilities are shown in FIG. 3(*b*), FIG. 3(*c*), FIG. 3(*d*), and FIG. 3(*e*).
Figure 3B:
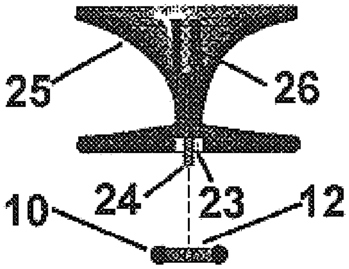
Figure 3C:
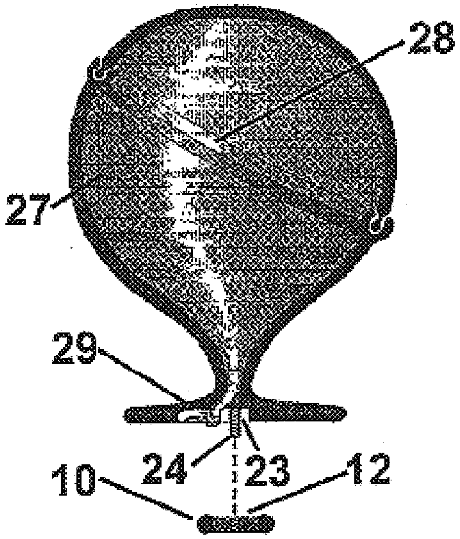
Figure 3D:
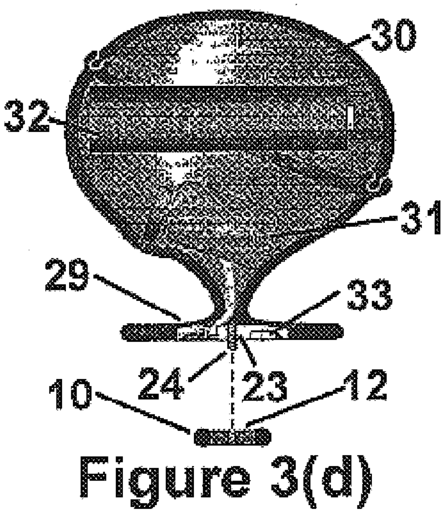
Figure 3E:
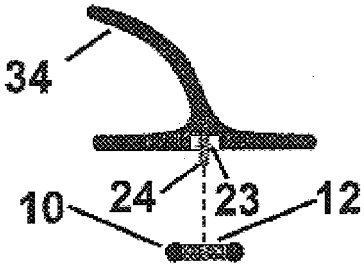

FIG. 2 shows a particular design for the frame in which it is constructed from stainless steel wire, with cross pieces for the extension attachment points, made of similar wire, welded in place as shown. In this figure one can see that the vaginal—insert attachment point is lowered below the level of the surrounding frame, while the anal—insert attachment point is raised above that surrounding level-both of which are done in order to accommodate the shape of the pelvis and its covering skin and the external vaginal lips.

FIG. 3(*a*) is a vertical-medial-plane, front-to-back cross-sectional view of just the central portion of the suit shown in FIG. 1. This shows the details of construction for this particular design of vaginal-insert extension, and its means of attachment to this particular design of frame. This extension (22) is formed as a hollow resilient bulb of soft rubber or plastic, with a skirt at the bottom end. The surface of the extension is soft, smooth, and washable to avoid any possibility of damage to the sensitive surfaces inside the vagina. These properties render it unlikely to retain harmful microorganisms and makes cleaning it very easy. When the extension is in place, the lower portion of the bulbous part bears on the inside of the muscular ring surrounding the vaginal opening, thus keeping the suit in close contact with the wearer's body. The bulb's skirt flares out over the frame-attachment mechanism, and protects the wearer from contact with that hard surface, plus it protects the suit from possible fluid leakage from the vagina.

Embedded at the center-bottom of the skirt on this design of vaginal-insert extension is a hard plastic disk (23) that has fixed in it a stainless steel threaded rod (24) that extends outside the disk a short distance. There is a port in the bottom of the skirt connected to the interior of the bulb, to permit squeezing out the air in the bulb during insertion or removal of the extension. The rod (24) screws into a stainless steel nut which is welded to the vaginal-insert attachment-support cross piece of the frame (10) to form the vaginal-insert attachment point (12). Other means of attaching and removing the extension [e.g., a quick-disconnect fitting] are, of course, possible and are also to be considered as covered by this patent application.

FIG. 3(*b*) shows one variation on this design for the vaginal-insert extension. This variation has the top of the bulb removed entirely. Thus, this extension (25) has a trumpet-like shape, which can be folded for insertion or removal, and which—while in the vagina—will flare out and bear on the inner surface of the ring of muscles surrounding the vaginal opening. [Such an extension does not have and would not need the exit port for air shown in FIG. 3(*a*).] The extension shown in FIG. 3(*b*) also has an (optional) socket (26) which could be used to retain a tampon, for use during a menstrual period, or for other purposes.

A young woman or girl might need a very small extension, whereas a woman who is sexually active might need a larger one, and a woman who has had several children might need a still larger one.

The vaginal-insert extension could be removable, as is shown here, or it could be formed as a part of the frame before insertion in the fabric which comprises the garment. The deciding factors will likely be cost of manufacture versus convenience and flexibility. If a garment accepts removable extensions, it can accept a range of them in different sizes and with different shapes or other features.

FIG. 3(*c*), shows another example of a vaginal-insert extension (27), in this instance one that is hollow and is provided with a reclosable opening (28). [In the design pictured in FIG. 3(*c*), the top of the bulbous part snaps off of the lower part, and when snapped in place, the two parts join along the line (28) with a water-tight seal.] Further, there is a valve (29) located on the underside of the extension's skirt, which valve can be operated by the wearer through the fabric covering of the suit. This valve permits one to expel the air inside the bulb to facilitate insertion of it, and then—after the bulb has expanded inside the wearer's body—to seal the bulb, so water cannot leak inside during swimming, for example. When it is time to remove the extension, the wearer can easily open the valve, once again permitting the bulb to be compressed easily during its withdrawal. This design could permit the wearer to store a few small objects [e.g., a key, ID, and some parking meter change] inside it and keep those items dry even while swimming.

Yet another design, based on the previous one—and shown here in FIG. 3(*d*) with a lower-profile bulb (30)—has a battery-operated vibrator (31) which, with its battery (32), is built into the bulbous part of the extension. A means of opening and resealing the bulb [similar to that shown in FIG. 3(*c*) as component (28)] permits replacing the battery as necessary. The base of the skirt has, as before, a valve (29) which can be opened to let air in or out, and which can be closed to exclude water. In addition, it also has an electrical switch (33)—operable from outside the suit, through the fabric covering—to permit the wearer to turn the vibrator on or off.

FIG. 3(*e*) shows yet another variation in the design of a vaginal-insert extension, in which the portion inside the vagina merely "hooks" onto the muscular ring surrounding the vaginal opening only on one side.

To reduce the frequency with which the extension must be cleaned, and to accommodate any user concerns about hygiene, the extension may be covered by a disposable, suitably formed "cot" [similar to a condom or finger cot, but differing in shape, as necessary]. This will be particularly important for pre-purchase trials of these garments.

Most, if not all, of the foregoing variations and comments regarding suitable materials and designs to be used also apply to any extension intended for insertion into a person's anus.

Figure 4:
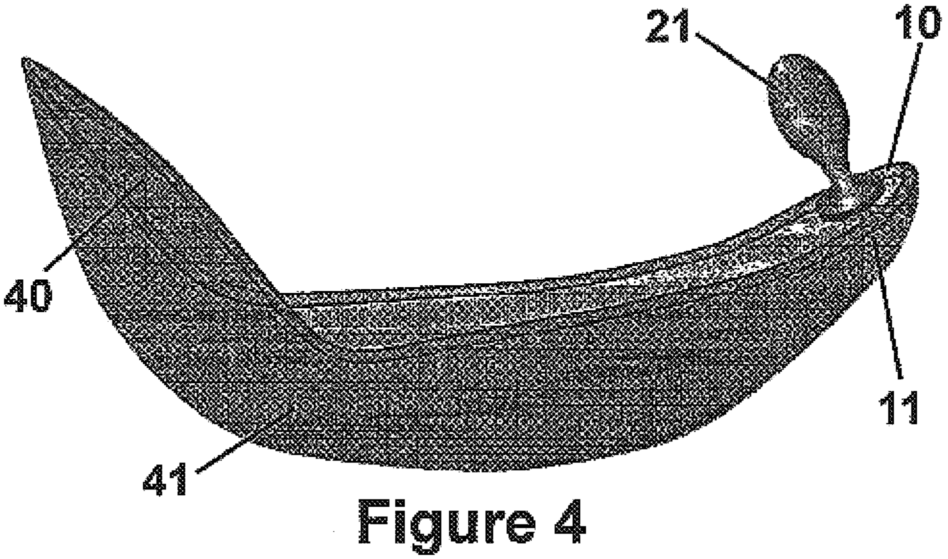
FIG. 4 shows the equivalent man's swimsuit—which, of necessity, uses an anal-insert extension, and also has various other differences from that in FIG. 1.

FIG. 4 is a drawing of a man's minimalist bathing suit. This is very similar to the design shown in FIG. 1, with the following differences, which are required to accommodate the man's different anatomy. First, the vaginal-insert cross piece with its extension attachment point (12) is missing from the frame (10). Second, the frame surrounds the testicles and penis [and, as before, it bears on the pelvis, and not against the insides of the legs]. Third, the insert (21) is designed for anal insertion and is attached to the anal-insert attachment point (11). Fourth, the fabric (40) is enlarged to form a pouch (41) of a sufficient size to accommodate the penis and testicles comfortably. The frame may (optionally) be extended upward on the front of the pelvis to a height above the end of the penis when it is engorged.

The anal-insert extension could be made available in various sizes, depending on the user's preference and experience. A short insert would be held in by the external sphincter, under voluntary control. A longer insert would also engage the higher-up, non-voluntarily controlled sphincter, which might give greater security from having the garment fall off, at the cost of greater difficulty of insertion. Disposable cots to cover the anal-insert extension would likely be desired at least as much as those to cover the vaginal-insert extensions.

Figure 5:
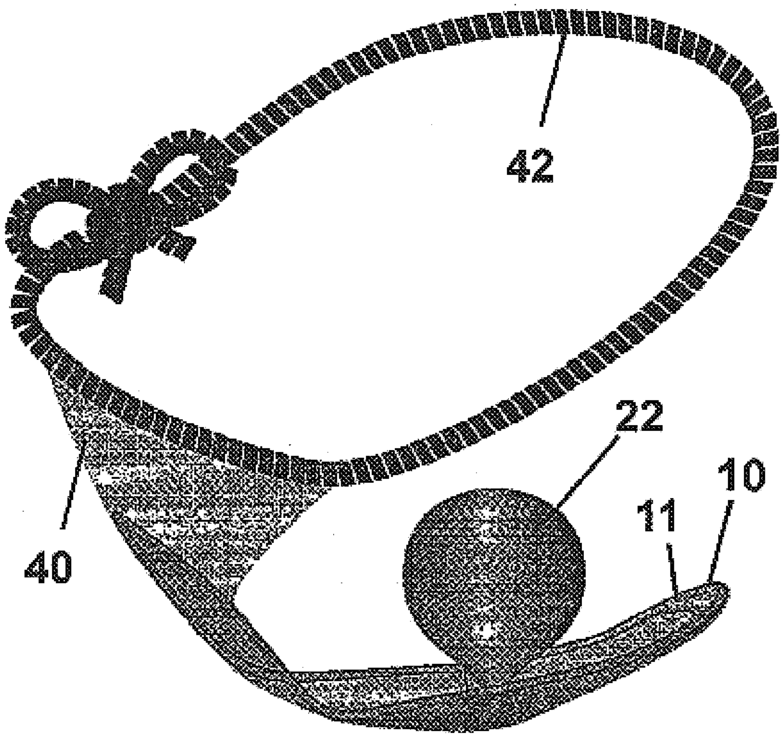
FIG. 5 shows a variation of the woman's garment in FIG. 1, this time adding additional material to the front panel and a cord around the waist.

FIG. 5 shows the swimsuit from FIG. 1 with the fabric covering (40) extended up toward the waist where it wraps around a cord or sash (42) that ties around the waist. [Similarly, the fabric itself could simply extend around the waist, as is often done in conventional swimsuits, without any opening in the waistband.] This would appear to the casual observer very much like an extreme thong or g-string swimsuit, but on careful examination it will be seen to lack the rear string or panel entirely.

Figure 6:
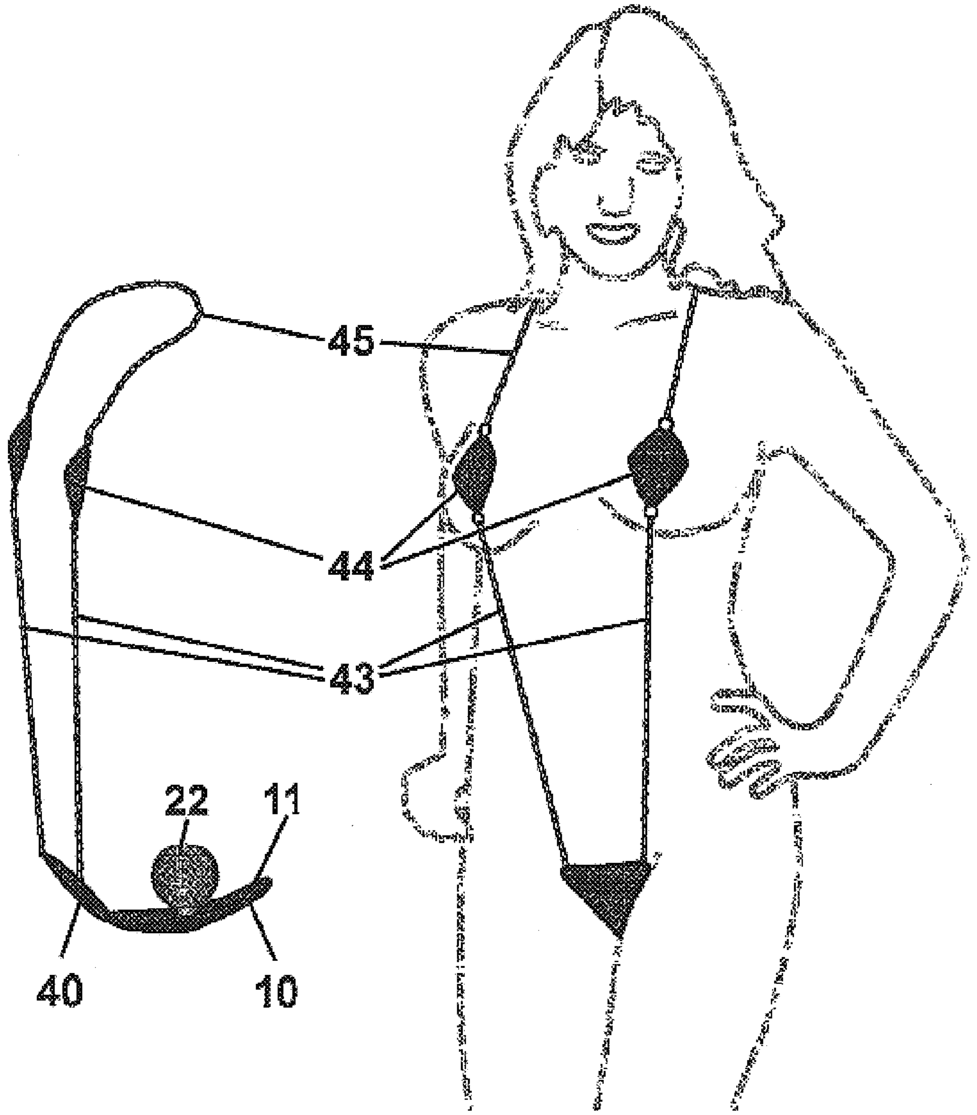
FIG. 6 shows another variation of the garment in FIG. 1, intended for a woman who wishes to expose her entire backside, but at least minimally cover her breasts as well as her genitals—and do so with a one-piece bathing suit.

FIG. 6 shows a different way of extending the swimsuit shown in FIG. 1. In this case the swimsuit has chains (43) attached to the top-front corners of the frame (10) [or, optionally, the chains could attach to the top of an extended fabric panel, much as the cord does in FIG. 5] and continuing upward to where they attach to smaller panels (44) that cover the nipples and areolae only [as shown in this figure], or that could be formed as full cups to hold the breasts. These panels or cups are then connected by another chain (45) going around the back of the neck. This design would give sufficient coverage in front and under the crotch to meet all the usual decency requirements, while presenting an appearance of total nudity from the rear. [The neck chain might appear to be a necklace, or if the woman has even moderately long hair, it would be covered completely in the rear.]

An obvious variation on this design would substitute fabric strips, which could be simply extensions of the fabric (40) that covers the frame at the crotch, for some or all of the chains.

Figure 7:
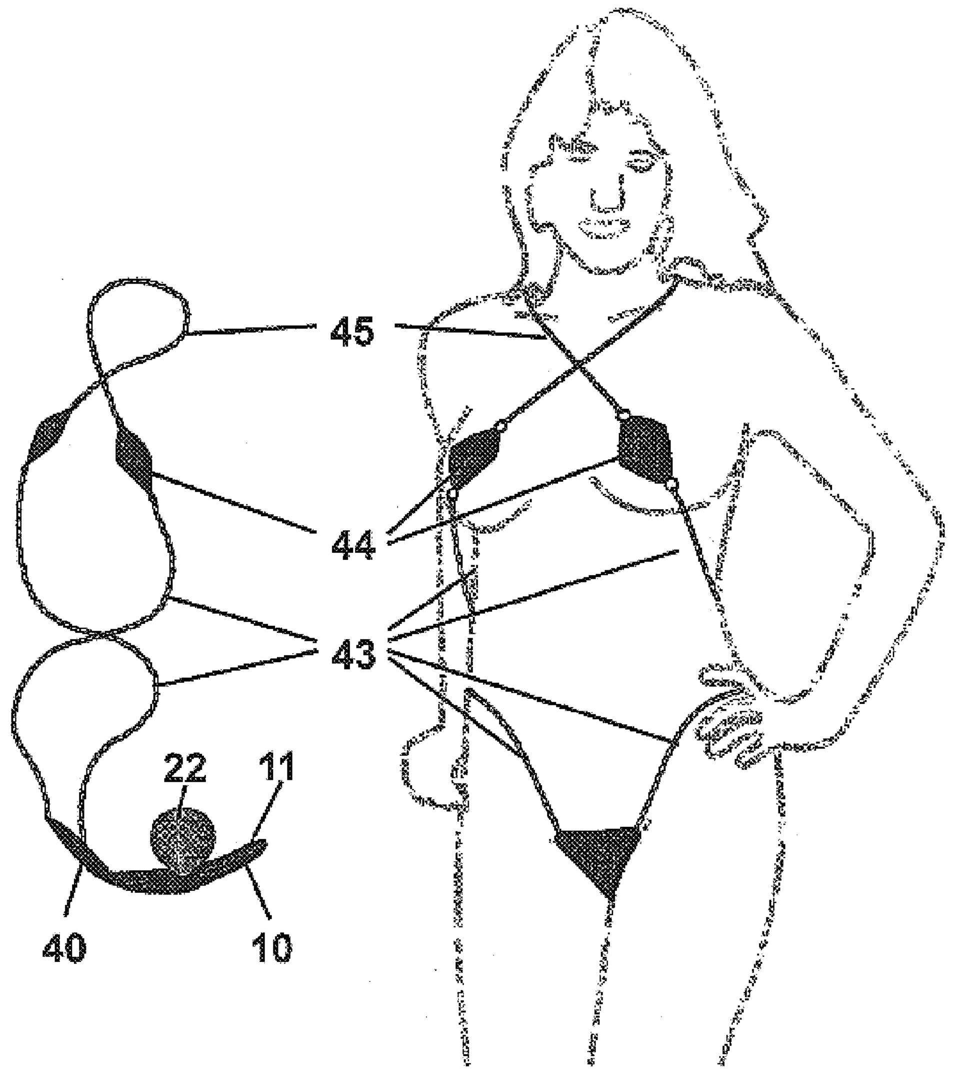
FIG. 7 shows yet another variation on the garment in FIG. 6, in this case including wrapping around the torso to ensure the suit's coverage of the breasts even during vigorous physical activity.

FIG. 7 shows a modification of the swimsuit in FIG. 6 in which the chains (43) [or fabric strips] connecting the bottom portion to the top wrap around the torso, and—to allow for the angle at which they then will connect to the bra portions (44)—the neck chain crosses in front of the throat, as well as going around the back of the neck. Optionally, the chains (43) could be replaced with transparent plastic straps, thus preserving the appearance from the rear of total nudity.

This design gives almost the same, full exposure as the previous one, plus it secures the bra panels much more firmly, thus permitting the wearer to engage in vigorous activities [swimming, beach volleyball, and the like] without fear of losing her decency-mandated body coverage.

A quite obvious group of other embodiments include underwear formed in a fashion quite similar to the swimsuits shown in FIG. 1 and FIG. 4, or with front panel extensions and waistbands [probably fabric instead of cord but otherwise as shown in FIG. 5]. One key advantage to women's and men's underpants resembling the swimsuits in FIG. 1 and FIG. 4, respectively—or the same designs but modified as shown in FIG. 5, using a flat fabric panel around the waist—is that their use would totally preclude the unsightly appearance of "visible panty lines" in tight pants or other garments worn over them.

Similarly, most conventional one-piece swimsuits could be modified by omitting the panel that covers the buttocks, and instead securing the lower front pelvis-covering panel under the crotch by use of this invention.

Thong, g-string and "slingshot" swimsuits and underwear could all be modified similarly, giving the benefit of no visible panty lines in underwear and greater exposure for swimwear. [The "slingshot" swimsuit is merely a thong with the sides raised over the shoulders, to give a sideless look—and sometimes with the front straps, so formed, covering the breasts. The modification contemplated here would join the two front straps behind the wearer's neck, and completely eliminate all of the rear portion of the suit.]

A "frontless" variation is also possible, in which the basic swimsuit shown in FIG. 1 has a fabric panel covering all or a portion of the buttocks before attaching to a waistband, but lacks any direct connection between the waistband and the front panel. Or the rear panel could go up the back, divide around the sides, and then connect to the bottom of breast cups or panels. This would create a swimsuit that looks much like that in FIG. 7, except that there would be no direct connection to the front of the bottom, and this design covers some or all of the buttocks.

A significant benefit of both swimwear and underwear utilizing this invention is that they permit the wearer to remove the swimsuit [or underpants] from the crotch region quickly and easily, thus permitting one to urinate and/or defecate without having to remove the entire suit. Furthermore, this can be done without having to lift either leg, thus allowing one to minimize the risk of falling over, and preclude having to lean on something as one removes or replaces one's swimsuit or underpants.

Other variations in the embodiments of this invention include backless slacks [not covering the buttocks and which, if provided with some transparent straps connecting around the back of the legs to hold the sides of the material covering the front of the legs, will appear not to have any back to the legs as well], a truly backless sundress, or even a backless formal gown or tuxedo, or any other type of garment that normally surrounds the pelvis.

Figure 8:
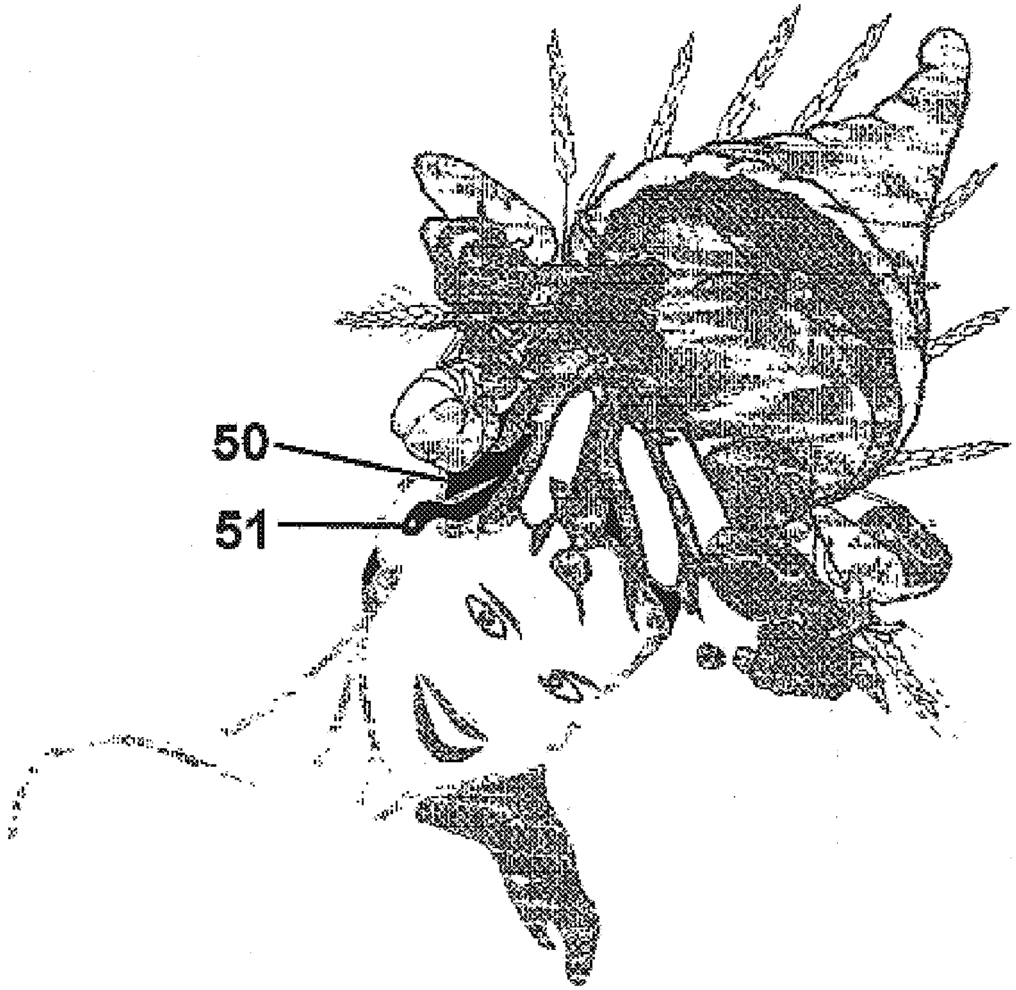
FIG. 8 shows a very different embodiment of this invention, in this case to a hat. Here a very top-heavy hat is balanced on the head, and is kept from slipping off by anchoring extensions that are snapped into the ears.

A possibly less-obvious additional embodiment is one that utilizes other orifices than the vagina or anus. FIG. 8 shows a woman wearing a very top-heavy headdress. Normally, such a large and top-heavy headdress is worn only by women who have shaved their heads or who have cut their hair very short. Those headdresses are conventionally built with a closely-fitted skull cap and scarf combination, with the scarf tying very tightly around the skull-in the process trapping and compressing the external ears, possibly quite painfully. And those headdresses are only able to stay in place if the wearer is very careful to hold her head very nearly vertical and to avoid any quick movements.

In contrast, the woman in FIG. 8 is shown with long hair and with her head tilted rather rakishly. This is possible because of the novel design of the headdress attachment. In addition to a reduced area skull cap (50), it includes two semi-rigid extensions (51) of that cap that extend out and down over the external ears and then inward where they snap into the ear canals. [These extensions may have holes in them to permit the wearer to hear more-or-less normally.]

With five or six bearing points [just in front of the crown of the head, on both sides of the rear base of the skull, in both ears, and possibly also just behind the crown] this headdress is quite securely held in place-even on a person having a great deal of hair-thus enabling its use by more people, minimizing the care the wearer must exercise, and permitting a wider range of motions. And it permits one to take the headdress on or off easily and quickly, simply by flexing the extensions (51) out to either side, then lifting the headdress on or off.

In all of the foregoing, any mention of fabric is intended to include alternative materials such as woven or non-woven fiber-based materials, real or imitation leather, plastic, wire mesh or fine chain mail, etc.

The foregoing description covers example embodiments, but it is not an exhaustive listing of all possible embodiments. Therefore, whereas many additional variations and modifications will readily occur to one skilled in the art, all such suitable modifications or variations are to be considered as falling within the scope of this invention.

I claim:

1. An article of clothing for a wearer's body, said article including an extension of a size, shape, and material adapted to insert said extension into one of the wearer's bodily orifices and thereby gaining a mechanical anchorage for said article sufficient in itself to maintain that portion of said article in place on the wearer's body in which said extension includes a watertight, reclosable storage cavity to retain and keep its contents dry.

2. An article of clothing as in claim 1 in which said extension contains a vibrator or other means to sexually stimulate the wearer.

3. An article of clothing as in claim 1 in which said extension's reclosable storage cavity has at a location on its exterior surface that will be within the vagina when it is inserted in the wearer's body and includes socket or other suitable means, at said location, for retaining a tampon or other, similar object that would otherwise be inserted inside the wearer's vagina.

* * * * *